United States Patent [19]
Guerrero et al.

[11] Patent Number: 5,425,939
[45] Date of Patent: Jun. 20, 1995

[54] THICKENED COSMETIC COMPOSITIONS

[75] Inventors: Angel A. Guerrero, Huntington; Thomas C. Klepacky, Shelton, both of Conn.

[73] Assignee: Elizabeth Arden Company, Division of Conopco, Inc., New York, N.Y.

[21] Appl. No.: 250,745

[22] Filed: May 27, 1994

[51] Int. Cl.$^6$ ............... A61K 31/78; A61K 7/48
[52] U.S. Cl. ............... 424/78.02; 424/59; 424/401; 424/78.18; 424/78.33; 514/844; 514/846; 514/847; 514/848
[58] Field of Search ............... 424/59, 78.02, 401, 424/78.18, 78.33; 514/844, 848

[56] References Cited

U.S. PATENT DOCUMENTS

| | | | |
|---|---|---|---|
| 3,659,025 | 4/1972 | Halleck | 424/361 |
| 3,915,921 | 10/1975 | Schlatzer, Jr. | 260/17.45 |
| 4,062,817 | 12/1977 | Westerman | 260/17.45 |
| 4,509,949 | 4/1985 | Huang et al. | 586/558 |
| 5,236,710 | 8/1993 | Guerrero et al. | 424/401 |

FOREIGN PATENT DOCUMENTS 2211192  6/1989  United Kingdom .

OTHER PUBLICATIONS

Harry's Cosmeticology, by Ralph G. Harry pp. 64–69 (1973).

*Primary Examiner*—Jyothsna Venkat
*Attorney, Agent, or Firm*—Milton L. Honig

[57] ABSTRACT

Thickened cosmetic compositions are provided based upon a thickening system that includes sclerotium gum and a hydrophobically-modified acrylate or methacrylate copolymer. The relative weight ratio of sclerotium gum to the polymer may range from about 1:1 to about 1:30. Compositions according to the present invention may also contain water-soluble vitamins. Interactive viscosity enhancement is particularly evident when free carboxylic groups present on the hydrophobically-modified acrylate or methacrylate copolymer are neutralized with a base thereby forming anionic carboxylate groups.

5 Claims, No Drawings

THICKENED COSMETIC COMPOSITIONS

BACKGROUND OF THE INVENTION

1. Field of the Invention

The invention relates to improved thickening systems for cosmetic compositions, particularly those in lotion and cream form.

2. The Related Art

Aqueous cosmetic compositions often require thickeners to achieve an aesthetically pleasing viscosity. Fluids that flow with a watery consistency too rapidly run off the treated skin areas. For a cosmetic to be effective, it often must have substantivity. Thickeners provide this substantivity. Furthermore, low viscosity formulas which may be skin effective nevertheless through their wateriness signal ineffectiveness to the consumer. Products of watery consistency are also aesthetically displeasing to consumers with expectations of rich and creamy products.

Countless numbers of thickening agents are known in the literature. Perhaps this plethora intimates that not all thickening agents are equally effective for any particular type of formulation.

Difficulties also arise in aqueous systems containing water-soluble vitamins. These function as electrolytes that adversely affect anionic polymeric thickening agents.

Indeed, there are some formulations which are extremely difficult to thicken, and even if initially thickened may have storage stability problems. Low pH systems are particularly sensitive and difficult.

Accordingly, it is an object of the present invention to provide a thickener system and thickened cosmetic compositions of sufficiently aesthetically pleasing viscosity.

It is another object of the present invention to provide a thickening system for a cosmetic composition that will be effective even in the presence of water-soluble vitamins which may function as electrolytes.

It is another object of the present invention to provide thickening systems for cosmetic compositions that are effective at low pH.

These and other objects of the present invention will more readily become apparent from the description and examples which follow.

SUMMARY OF THE INVENTION

A cosmetic composition is provided which includes:
(i) from 0.005 to 1% of sclerotium gum;
(ii) from 0.005 to 1% of a hydrophobically-modified acrylate or methacrylate copolymer; and
(iii) a cosmetically acceptable carrier.

Compositions according to the present invention may also contain water-soluble vitamins. Moreover, the thickening system is particularly effective at a pH between about 6.8 and 1. Interactive viscosity enhancement is particularly evident when free carboxylic groups present on the hydrophobically-modified acrylate or methacrylate copolymer are neutralized with a base thereby forming anionic carboxylate groups.

DETAILED DESCRIPTION OF THE INVENTION

Now it has been discovered that sclerotium gum in combination with a hydrophobically-modified acrylate or methacrylate polymer combine to form a highly effective thickening system for cosmetic compositions. This system is particularly useful for building viscosity in compositions containing electrolytes.

Accordingly, a first critical element of compositions according to the present invention is that of sclerotium gum (CTFA name), a polymerized glucose. This capsular β-D-glucan can be produced from a variety of fungi grown in media containing either glucose or sucrose as carbon sources and complex nitrogen sources supplemented with mineral salts. Glucan with an estimated degree of polymerization around 100 is obtained with *Sclerotium glucanicum* or with degree of polymerization around 800 from a strain of *Sclerotium rolfsii*. Aside from the degree of polymerization, the various sclerotium gums differ slightly in number and length of side chains. These gums can be prepared through aerobic, submerged fermentation at 30° C. for 60 hours to achieve a pelletlike growth shrouded by a capsule. The capsule is an extended gel phase that is largely immiscible with water. The culture is heated to inactivate glucanase activity and to kill the organism which is a plant pathogen. Homogenization of the culture frees the gum from the mycelia and converts the polysaccharide to a form that is readily dispersible from the dried state. Commercially, a sclerotium gum derived from *Sclerotium rolfsii* is available under the trademark Amigel from Alban Muller/Tri K France. Amounts of this material may range from about 0.005 to about 1%, preferably from about 0.01 to about 0.5%, optimally from about 0.05 to about 0.3% by weight.

A second essential element of the compositions according to the present invention is that of a hydrophobically-modified acrylate or methacrylate polymer. The polymer is preferably a copolymer formed from about 50 to 99% by weight of a monoolefinically unsaturated carboxylic acid or anhydride monomer of 3 to 6 carbon atoms and from about 1 to 50% by weight of a long chain $C_{10}$–$C_{30}$ acrylate or methacrylate ester monomer. Optionally, there is included in the monomeric mixture a crosslinking monomer. In a preferred embodiment, amount of the carboxylic monomer is 80 to 99%, but especially 90 to 98% by weight, whereas amount of the acrylate monomer is from 20 down to 1%, especially 10 down to 2% by weight, based on the weight of the two monomers. Amounts of the carboxylic monomer and the acrylate ester monomer are based on the combined weight of both components. It should be understood that more than one carboxylic monomer and more than one acrylate ester can be utilized to form the copolymer.

The preferred acrylic ester monomers having long chain aliphatic groups are derivatives of acrylic acid represented by the formula:

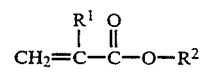

wherein $R^1$ is selected from hydrogen, methyl and ethyl groups and $R^2$ is selected from alkyl groups having from 10 to 30 carbon atoms and oxyalkylene and carbonyloxyalkylene groups, preferably alkyl groups of 10 to 22 carbon atoms. The oxyalkylene and carbonyloxyalkylene groups are particularly oxyethylene and carbonyloxyethylene groups. Representative higher alkyl acrylic esters are decyl acrylate, lauryl acrylate, stearyl acrylate, behenyl acrylate and myristyl acrylate, and the corresponding methacrylates.

Structures and syntheses of the hydrophobically-modified acrylate or methacrylate polymer can be found in U.S. Pat. No. 3,915,921 (Schlatzer, Jr.), U.S. Pat. No. 4,062,817 (Westerman) and U.S. Pat. No. 4,509,949 (Huang et al.), all of which are herewith incorporated by reference.

For purposes of the present invention, the hydrophobically-modified copolymer may be neutralized with a base to convert the free carboxylic acid groups pendent from the copolymer into their respectively neutralized salts. Suitable neutralization agents are alkali metal bases such as sodium hydroxide, potassium hydroxide and lithium hydroxide. Organic amine type bases may also be employed, the most preferable of which is triethanolamine.

Commercially, the hydrophobically-modified copolymer as described above is available from the B.F. Goodrich Company under the trademark Carbopol 1382®. The CTFA name is acrylates/$C_{10}$-$C_{30}$ alkyl acrylate cross-polymer.

Amounts of the hydrophobically-modified acrylate or methacrylate polymer will range from about 0.005 to about 1%, preferably from about 0.01 to about 0.5%, more preferably from about 0.1 to about 0.3% by weight.

Relative weight ratios of sclerotium gum to hydrophobically-modified acrylate or methacrylate copolymer will range from about 1:1 to about 1:30, preferably from about 1:2 to about 1:10, optimally from about 1:3 to about 1:5 by weight.

Compositions of the present invention may include an aqueous phase or be totally aqueous. Advantageously the pH of such aqueous systems may range from about 8.0 down to 1.0, preferably ranging from about 6.8 to about 4, optimally between about 5.5 and 5.

Compositions of the present invention may also contain water-soluble vitamins, which may function as electrolytes. The term water-soluble defines substances with a solubility of at least 0.1%, preferably at least 1%, optimally at least 5% by weight in water. Illustrative water-soluble vitamins are Niacin, Vitamin $B_2$, Vitamin $B_6$, Vitamin C and Biotin. One source for Vitamin C is a product sold under the trademark of Vitazyme C available from the Brooks Company. Niacin, Vitamin B and Biotin are available from Roche Pharmaceuticals. Total amount of vitamins in compositions according to the present invention may range from about 0.001 to about 1%, preferably from about 0.01 to about 0.6, optimally from about 0.1 to about 0.5% by weight.

Two classes of keratolytic agents may also be effectively used in compositions of the present invention. The first category is represented by $C_7$-$C_{30}$ $\beta$-hydroxy carboxylic acids and their salts. Illustrative of this category is salicylic acid as well as the alkalimetal and ammonium salts thereof. Suitable amounts of salicylic acid or salt may range from about 0.001 to about 10%, preferably between about 0.8 and about 2.5%, optimally between about 1 and 1.5% by weight.

The second class of keratolytic agent is the $C_2$-$C_{25}$ $\alpha$-hydroxy alkanoic acids. Illustrative of this group of materials are glycolic, lactic, $\alpha$-hydroxyoctanoic acids and salts thereof. The salts may be selected from alkalimetal, ammonium and $C_1$-$C_{20}$ alkyl or alkanolammonium counterions. Levels of $\alpha$-hydroxyalkanoic acids may range from about 0.001 to about 10%, preferably between about 0.2 and 1%, optimally between about 0.4 and 0.5% by weight.

Compositions of the present invention may either be aqueous or anhydrous. Preferably the compositions are aqueous, especially water and oil emulsions of the W/O or O/W variety. Water when present will be in amounts which may range from about 5 to about 90%, preferably from about 35 to about 65%, optimally between about 40 and 50% by weight.

Besides water, relatively volatile solvents may also be incorporated within compositions of the present invention. Most preferred are monohydric $C_1$-$C_3$ alkanols. These include ethyl alcohol, methyl alcohol and isopropyl alcohol. The amount of monohydric alkanol may range from about 5 to about 50%, preferably from about 15 to about 40%, optimally between about 25 to about 35% by weight.

Emollient materials in the form of silicone oils and synthetic esters may be incorporated into compositions of the present invention. Amounts of the emollients may range anywhere from about 0.1 to about 30%, preferably between about 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate.
(5) Sterols esters, of which cholesterol fatty acid esters are examples thereof.

The most preferred esters are octyldodecyl neopentanoate (available as Elefac I-205 ®) and isononyl isononanoate.

Fatty acids having from 10 to 30 carbon atoms may also be included in the compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Collectively the water, solvents, silicones, esters, fatty acids, humectants and/or thickeners are viewed as cosmetically acceptable carriers for the compositions of the invention. Total amount of carrier will range from about 1 to 99.9%, preferably from about 80 to 99% by weight.

Cosmetic compositions of the present invention may be in any form. These forms may include lotions, creams, roll-on formulations, mousses, aerosol sprays and pad-applied formulations.

Surfactants may also be present in cosmetic compositions of the present invention. Total concentration of the surfactant will range from about 0.1 to about 40%, preferably from about 1 to about 20%, optimally from about 1 to about 5% by weight of the total composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di- fatty acid esters of ethylene glycol; fatty acid monoglyceride; sorbitan, mono- and di- $C_8$-$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates and combinations thereof.

Sunscreen actives may also be included in compositions of the present invention. Particularly preferred are such materials as ethylhexyl p-methoxycinnamate, available as Parsol MCX, and benzophenone-3, also known as Oxybenzone. Inorganic sunscreen actives may be employed such as microfine titanium dioxide, polyethylene and various other polymers. Amounts of the sunscreen agents will generally range from about 0.1 to about 30%, preferably from about 2 to about 20%, optimally from about 4 to about 10% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Minor adjunct ingredients may also be present in the cosmetic compositions. Among them may be the water-insoluble vitamins such as Vitamin A Palmitate, Vitamin E Acetate and DL-panthenol.

Another adjunct ingredient can be that of an enzyme. Particularly preferred is superoxide dismutase, commercially available as Biocell SOD from the Brooks Company, USA.

Natural vegetable materials from renewable resources are often desirable in cosmetic compositions. For instance, cosmetic compositions of the present invention may include β-glucan derived from oats, commercially available under the trademark Microat SF from Nurture Inc., Missoula, Mont.

Colorants, fragrances, opacifiers and abrasives may also be included in compositions of the present invention. Each of these substances may range from about 0.05 to about 5%, preferably between 0.1 and 3% by weight.

The following Examples will more fully illustrate the embodiments of this invention. All parts, percentages and proportions referred to herein and in the appended claims are by weight unless otherwise indicated.

EXAMPLES 1–4

The following experiments were conducted to demonstrate the interactive effect of Amigel ® and Carbopol 1382 ®. Four formula sets were evaluated. Two of the sets were conducted on unneutralized Carbopol 1382 ® and two were conducted on neutralized (with triethanolamine) Carbopol 1382 ®. Sets 2 and 4 were further formulated with 0.512% of an aqueous vitamin composition that included 0.2% Niacin, 0.1% Vitamin $B_6$, 0.01% Biotin, 0.001% Biocell S.O.D. (Superoxide Dismutase), 0.001% Vitazyme C and 0.2% DL-panthenol.

Each formula set was further subdivided into five combinations (ratios) of Carbopol 1382 ® and Amigel ®. Each of the samples were stored in an oven at 25° C., 43° C. and under alternating temperature (4° C.–43° C.). Brookfield viscosities (spindle no. 3 at 20 rpm at 25° C.) and pH were measured for each of the samples. These measurements were conducted over one month at one week intervals.

Tables I–IV list the results of the viscosity and pH measurements for the respective formula sets 1–4.

Based on the results listed in these tables, it is evident that enhanced viscosity is achieved by combination of Amigel® and Carbopol 1382® over samples only containing a single thickener. This is seen from a comparison of samples 1-C and 1-D versus the separate thickeners in 1-A and 1-B.

The presence of vitamins (i.e. electrolytes) significantly affected viscosity of Carbopol 1382®. Best results were achieved with samples 4-C when compared to the individual thickeners 4-A and 4-B.

| FORMULA SET | CARBOPOL 1382 ® | VITAMINS (0.512%) |
|---|---|---|
| 1 | unneutralized | none |
| 2 | unneutralized | yes |
| 3 | neutralized (TEA) | none |
| 4 | neutralized (TEA) | yes |

| THICKENER CODE | THICKENERS (% IN TEST SAMPLE) |
|---|---|
| A | 0.1% Amigel ® |
| B | 0.36% Carbopol 1382 ® |
| C | 0.1% Amigel ® and 0.36% Carbopol 1382 ® |
| D | 0.2% Amigel ® and 0.02% Carbopol 1382 ® |
| E | 0.02% Amigel ® and 0.2% Carbopol 1382 ® |

TABLE I

| SAMPLES | 25° C. pH | 25° C. Viscosity | ALT pH | ALT Viscosity | 43° C. pH | 43° C. Viscosity |
|---|---|---|---|---|---|---|
| 1 WEEK | | | | | | |
| 1-A | 4.97 | 20.00 | 6.41 | 20.00 | 6.66 | 25.00 |
| 1-B | 3.25 | 45.00 | 3.16 | 40.00 | 3.13 | 45.00 |
| 1-C | 3.40 | 85.00 | 3.33 | 95.00 | 3.25 | 90.00 |
| 1-D | 4.78 | 65.00 | 4.85 | 75.00 | 4.87 | 80.00 |
| 1-E | 3.45 | 25.00 | 3.43 | 25.00 | 3.48 | 25.00 |
| 2 WEEKS | | | | | | |
| 1-A | 5.63 | 20.00 | 5.71 | 25.00 | 6.52 | 20.00 |
| 1-B | 3.30 | 40.00 | 3.29 | 45.00 | 3.27 | 45.00 |
| 1-C | 3.27 | 95.00 | 3.30 | 100.00 | 3.30 | 125.00 |
| 1-D | 4.54 | 70.00 | 4.80 | 85.00 | 4.80 | 90.00 |
| 1-E | 3.43 | 25.00 | 3.51 | 25.00 | 3.53 | 25.00 |
| 3 WEEKS | | | | | | |
| 1-A | 5.58 | 20.00 | 6.24 | 20.00 | 6.98 | 20.00 |
| 1-B | 3.23 | 40.00 | 3.23 | 40.00 | 3.23 | 40.00 |
| 1-C | 3.26 | 100.00 | 3.27 | 105.00 | 3.26 | 135.00 |
| 1-D | 4.58 | 70.00 | 4.73 | 70.00 | 4.74 | 95.00 |
| 1-E | 3.44 | 25.00 | 3.44 | 25.00 | 3.45 | 25.00 |
| 1 MONTH | | | | | | |
| 1-A | 5.60 | 20.00 | 6.25 | 25.00 | 7.00 | 25.00 |
| 1-B | 3.25 | 50.00 | 3.25 | 55.00 | 3.25 | 60.00 |
| 1-C | 3.25 | 110.00 | 3.25 | 130.00 | 3.25 | 150.00 |
| 1-D | 4.60 | 75.00 | 4.75 | 90.00 | 4.75 | 100.00 |
| 1-E | 3.45 | 20.00 | 3.45 | 50.00 | 3.45 | 30.00 |

TABLE II

| SAMPLES | 25° C. pH | 25° C. Viscosity | ALT pH | ALT Viscosity | 43° C. pH | 43° C. Viscosity |
|---|---|---|---|---|---|---|
| 1 WEEK | | | | | | |
| 2-A | 3.44 | 25.00 | 3.44 | 25.00 | 3.46 | 25.00 |
| 2-B | 3.06 | 20.00 | 3.12 | 20.00 | 3.17 | 20.00 |
| 2-C | 3.21 | 35.00 | 3.20 | 40.00 | 3.21 | 40.00 |
| 2-D | 3.50 | 55.00 | 3.50 | 65.00 | 3.51 | 65.00 |
| 2-E | 3.30 | 20.00 | 3.24 | 20.00 | 3.28 | 20.00 |
| 2 WEEKS | | | | | | |
| 2-A | 3.42 | 25.00 | 3.45 | 25.00 | 3.50 | 25.00 |
| 2-B | 3.11 | 20.00 | 3.22 | 20.00 | 3.27 | 20.00 |
| 2-C | 3.19 | 35.00 | 3.23 | 40.00 | 3.27 | 50.00 |
| 2-D | 3.47 | 55.00 | 3.50 | 65.00 | 3.60 | 70.00 |
| 2-E | 3.25 | 20.00 | 3.30 | 20.00 | 3.36 | 20.00 |
| 3 WEEKS | | | | | | |
| 2-A | 3.25 | 25.00 | 3.27 | 25.00 | 3.53 | 25.00 |
| 2-B | 3.22 | 15.00 | 3.22 | 20.00 | 3.25 | 20.00 |
| 2-C | 3.22 | 30.00 | 3.22 | 40.00 | 3.27 | 50.00 |
| 2-D | 3.50 | 55.00 | 3.51 | 70.00 | 3.53 | 75.00 |
| 2-E | 3.25 | 20.00 | 3.31 | 20.00 | 3.36 | 20.00 |
| 1 MONTH | | | | | | |
| 2-A | 3.25 | 20.00 | 3.25 | 25.00 | 3.50 | 25.00 |
| 2-B | 3.20 | 20.00 | 3.20 | 20.00 | 3.20 | 20.00 |
| 2-C | 3.20 | 35.00 | 3.20 | 45.00 | 3.25 | 50.00 |
| 2-D | 3.50 | 60.00 | 3.50 | 65.00 | 3.50 | 75.00 |

TABLE III

| SAMPLES | 25° C. pH | 25° C. Viscosity | ALT pH | ALT Viscosity | 43° C. pH | 43° C. Viscosity |
|---|---|---|---|---|---|---|
| 1 WEEK | | | | | | |
| 3-A | 8.16 | 20.00 | 8.33 | 25.00 | 8.35 | 25.00 |
| 3-B | 5.90 | 32,000.00 | 5.91 | 31,500.00 | 5.88 | 31,400.00 |
| 3-C | 6.27 | 46,600.00 | 6.45 | 46,800.00 | 6.26 | 45,300.00 |
| 3-D | 7.84 | 160.00 | 8.24 | 150.00 | 8.27 | 180.00 |
| 3-E | 6.50 | 25,400.00 | 6.40 | 24,700.00 | 6.33 | 24,400.00 |
| 2 WEEKS | | | | | | |
| 3-A | 7.32 | 20.00 | 7.94 | 25.00 | 8.33 | 25.00 |
| 3-B | 5.99 | 30,600.00 | 6.03 | 31,400.00 | 5.92 | 30,900.00 |
| 3-C | 6.36 | 45,100.00 | 6.45 | 44,700.00 | 6.41 | 43,000.00 |
| 3-D | 7.68 | 150.00 | 7.92 | 150.00 | 8.16 | 200.00 |
| 3-E | 6.18 | 25,700.00 | 6.23 | 24,700.00 | 6.19 | 24,000.00 |
| 3 WEEKS | | | | | | |
| 3-A | 7.35 | 20.00 | 7.81 | 25.00 | 8.17 | 25.00 |
| 3-B | 6.03 | 31,500.00 | 6.07 | 30,900.00 | 6.03 | 30,400.00 |
| 3-C | 6.23 | 42,600.00 | 6.29 | 44,700.00 | 6.28 | 40,700.00 |
| 3-D | 7.70 | 150.00 | 8.04 | 155.00 | 8.29 | 200.00 |
| 3-E | 6.27 | 25,200.00 | 6.28 | 24,100.00 | 6.25 | 23,400.00 |
| 1 MONTH | | | | | | |
| 3-A | 7.35 | 20.00 | 7.80 | 25.00 | 8.20 | 25.00 |
| 3-B | 6.00 | 31,200.00 | 6.05 | 30,800.00 | 6.05 | 30,600.00 |
| 3-C | 6.25 | 44,500.00 | 6.30 | 44,700.00 | 6.30 | 42,600.00 |
| 3-D | 7.70 | 30.00 | 8.05 | 185.00 | 8.30 | 225.00 |
| 3-E | 6.25 | 24,100.00 | 6.30 | 24,800.00 | 6.25 | 23,500.00 |

TABLE IV

| SAMPLES | 25° C. pH | 25° C. Viscosity | ALT pH | ALT Viscosity | 43° C. pH | 43° C. Viscosity |
|---|---|---|---|---|---|---|
| 1 WEEK | | | | | | |
| 4-A | 4.26 | 25.00 | 4.26 | 25.00 | 4.23 | 25.00 |
| 4-B | 4.74 | 4,000.00 | 4.72 | 3,400.00 | 4.82 | 3,700.00 |
| 4-C | 5.18 | 9,600.00 | 5.17 | 9,500.00 | 5.20 | 9,900.00 |
| 4-D | 5.01 | 65.00 | 5.13 | 80.00 | 5.12 | 80.00 |
| 4-E | 4.51 | 75.00 | 4.51 | 75.00 | 4.53 | 80.00 |
| 2 WEEKS | | | | | | |
| 4-A | 4.15 | 20.00 | 4.19 | 25.00 | 4.19 | 25.00 |
| 4-B | 4.88 | 3,900.00 | 4.89 | 3,400.00 | 4.84 | 3,600.00 |
| 4-C | 5.24 | 9,600.00 | 5.23 | 9,300.00 | 5.21 | 9,400.00 |
| 4-D | 4.30 | 75.00 | 4.84 | 80.00 | 4.89 | 95.00 |
| 4-E | 4.44 | 75.00 | 4.53 | 80.00 | 4.45 | 80.00 |
| 3 WEEKS | | | | | | |
| 4-A | 4.19 | 25.00 | 4.22 | 25.00 | 4.23 | 25.00 |
| 4-B | 4.94 | 4,000.00 | 4.86 | 3,500.00 | 4.84 | 3,800.00 |
| 4-C | 5.21 | 9,000.00 | 5.21 | 9,800.00 | 5.21 | 1,010.00 |
| 4-D | 4.86 | 65.00 | 4.91 | 80.00 | 4.19 | 95.00 |
| 4-E | 4.52 | 75.00 | 4.53 | 80.00 | 4.52 | 80.00 |

TABLE IV-continued

| SAMPLES | 25° C. pH | 25° C. Viscosity | ALT pH | ALT Viscosity | 43° C. pH | 43° C. Viscosity |
|---|---|---|---|---|---|---|
| MONTH | | | | | | |
| 4-A | 4.20 | 25.00 | 4.20 | 25.00 | 4.25 | 25.00 |
| 4-B | 4.95 | 4,000.00 | 4.85 | 360.00 | 4.85 | 4,200.00 |
| 4-C | 5.20 | 9,100.00 | 5.20 | 9,800.00 | BROKEN | BROKEN |
| 4-D | 4.85 | 60.00 | 4.90 | 85.00 | 4.90 | 100.00 |
| 4-E | 4.50 | 75.00 | 4.55 | 65.00 | 4.50 | 85.00 |

EXAMPLE 5

A typical fully formulated sunscreen lotion according to the present invention is described in Table V.

TABLE V

| COMPONENT | WEIGHT % |
|---|---|
| Carbopol 1382 ® (2% active) | 8.000 |
| Cyclomethicone | 6.000 |
| Parsol MCX ® | 6.000 |
| Isoarachidyl Neopentanoate | 4.300 |
| Benzophenone-3 | 3.000 |
| Glycerin | 3.000 |
| Isononyl Isononanoate | 2.500 |
| Arlacel 165 VS ® (GMS/PEG) | 1.700 |
| BRIJ 721 ® (Vegetable) | 1.200 |
| Isostearic Acid | 1.200 |
| Polymethyl Methacrylate | 1.000 |
| Cetyl Alcohol | 1.000 |
| Triethanolamine | 0.770 |
| Phenoxyethanol | 0.700 |
| Actiglyde-J Special ® (Bio-hyaluronic acid) | 0.500 |
| Vitamin E Acetate | 0.500 |
| BRIJ 72 ® (Vegetable) | 0.300 |
| Methylparaben | 0.300 |
| Polyethylene (A-C 400) | 0.300 |
| Algae Extract | 0.250 |
| Glydant ® | 0.200 |
| DL-Panthenol | 0.200 |
| $C_{12}$–$C_{20}$ Acid-PEG 8 Esters | 0.200 |
| Trilaureth-4-Phosphate | 0.200 |
| Silicone 200 (10 cst) | 0.200 |
| Microat SF ® | 0.200 |
| Niacin | 0.200 |
| Amigel ® | 0.170 |
| Vitazyme C ® | 0.100 |
| Superoxide Dismutase | 0.100 |
| Vitamin $B_6$ | 0.100 |
| Vitamin A Palmitate | 0.100 |
| Propylparaben | 0.100 |
| Disodium EDTA | 0.100 |
| l-Lactic Acid | 0.010 |
| Biotin | 0.001 |
| Deionized Water | qs |

EXAMPLE 6

A typical fully formulated creme according to the present invention is described in Table VI.

TABLE VI

| COMPONENT | WEIGHT % |
|---|---|
| Carbopol 1382 ® (2% Active) | 18.000 |
| Cyclomethicone | 6.000 |
| Cetyl Alcohol | 4.400 |
| Spectron SA-13 ® | 4.000 |
| Glycerin | 3.000 |
| Isoarachidyl Neopentanoate | 2.400 |
| Emulgade 100 NI ® | 1.750 |
| Willowbark Extract | 1.500 |
| Triethanolamine 99% | 1.420 |
| $C_{18}$–$C_{36}$ Fatty Acid | 1.200 |
| BRIJ 721 ® (Vegetable) | 1.200 |
| Arachidyl Behenate | 1.000 |
| Actiglyde-J Special ® | 1.000 |
| Polymethyl Methacrylate | 1.000 |
| Vitamin E Acetate | 1.000 |
| Sodium Pyrollidone Carboxylate (50% active) | 0.750 |
| Algae Extract | 0.500 |
| DL-Panthenol | 0.500 |
| Silicone 200 (10 cst) | 0.400 |
| $C_{12}$–$C_{21}$ Acid-PEG 8 Esters | 0.400 |
| Microat SF ® | 0.360 |
| Bernel Ester TOC ® | 0.360 |
| Glydant ® | 0.300 |
| Methylparaben | 0.300 |
| BRIJ 72 ® (Vegetable) | 0.300 |
| Polyethylene (A-C 400) | 0.300 |
| Shea Butter | 0.200 |
| Disodium EDTA | 0.100 |
| Amigel ® | 0.100 |
| Propylparaben | 0.100 |
| Vitamin A Acetate | 0.100 |
| l-Lactic Acid | 0.010 |
| Biotin | 0.001 |
| Vitazyme C ® | 0.001 |
| Deionized Water | qs |

The foregoing description and Examples illustrate selected embodiments of the present invention. In light thereof, various modifications will be suggested to one skilled in the art, all of which are within the spirit and purview of this invention.

What is claimed is:

1. A cosmetic composition comprising:
   (i) from about 0.05 to about 0.3% of sclerotium gum;
   (ii) from about 0.1 to about 0.5% of a hydrophobically-modified acrylate or methacrylate copolymer formed in an amount from about 50 to 99% by weight of a monoolefinically unsaturated carboxylic acid or anhydride monomer of 3 to 6 carbon atoms and in an amount from about 1 to about 50% by weight formed from a long chain acrylate or methacrylate ester monomer; and
   (iii) from 1 to 99.9% of a cosmetically acceptable carrier.

2. A composition according to claim 1 wherein the hydrophobically-modified acrylate or methacrylate copolymer has all of its free carboxylic acid groups neutralized.

3. A composition according to claim 2 wherein neutralization occurs by treatment of the copolymer with an alkaline base selected from the group consisting of sodium hydroxide, potassium hydroxide, lithium hydroxide and triethanolamine.

4. A composition according to claim 1 further comprising from about 0.001 to about 1% by weight of water-soluble vitamins.

5. A composition according to claim 4 wherein the vitamins are selected from the group consisting of Niacin, Vitamin $B_6$, Vitamin $B_2$, Biotin, Vitamin C and mixtures thereof.

* * * * *